United States Patent
Yang et al.

(10) Patent No.: US 11,524,054 B2
(45) Date of Patent: Dec. 13, 2022

(54) METHOD OF TREATING ANEMIA USING LONG-ACTING EPO FORMULATION

(71) Applicants: GENEXINE, INC., Seongnam-si (KR); GREEN CROSS CORPORATION, Yongin-si (KR)

(72) Inventors: Sang-In Yang, Daegu (KR); Jung-Won Woo, Seoul (KR); Se Hwan Yang, Seoul (KR); Young Chul Sung, Seoul (KR); Doo Hong Park, Seoul (KR); Min Woo Kim, Seoul (KR)

(73) Assignees: GENEXINE, INC., Seongnam-si (KR); GREEN CROSS CORPORATION, Yongin-si (KR)

( * ) Notice: Subject to any disclaimer, the term of this patent is extended or adjusted under 35 U.S.C. 154(b) by 0 days.

(21) Appl. No.: 15/542,172

(22) PCT Filed: Jan. 8, 2016

(86) PCT No.: PCT/KR2016/000175
§ 371 (c)(1),
(2) Date: Jul. 7, 2017

(87) PCT Pub. No.: WO2016/111575
PCT Pub. Date: Jul. 14, 2016

(65) Prior Publication Data
US 2018/0264082 A1    Sep. 20, 2018

Related U.S. Application Data

(60) Provisional application No. 62/101,639, filed on Jan. 9, 2015.

(51) Int. Cl.
| | | |
|---|---|---|
| *A61K 39/00* | (2006.01) | |
| *C07K 16/46* | (2006.01) | |
| *A61K 38/18* | (2006.01) | |
| *C07K 19/00* | (2006.01) | |
| *A61K 38/16* | (2006.01) | |
| *A61P 7/06* | (2006.01) | |
| *A61K 9/00* | (2006.01) | |
| *A61K 38/17* | (2006.01) | |
| *C07K 16/00* | (2006.01) | |

(52) U.S. Cl.
CPC ........ *A61K 38/1816* (2013.01); *A61K 9/0019* (2013.01); *A61K 38/16* (2013.01); *A61K 38/1774* (2013.01); *A61K 38/18* (2013.01); *A61P 7/06* (2018.01); *C07K 19/00* (2013.01); *A61K 39/00* (2013.01); *C07K 16/00* (2013.01); *C07K 16/46* (2013.01)

(58) Field of Classification Search
None
See application file for complete search history.

(56) References Cited

U.S. PATENT DOCUMENTS

| | | | |
|---|---|---|---|
| 7,867,491 B2 | 1/2011 | Yang et al. | |
| 2004/0132645 A1* | 7/2004 | Knox | A61K 38/1816 |
| | | | 514/7.7 |
| 2007/0178112 A1* | 8/2007 | Wang | C07K 14/505 |
| | | | 424/178.1 |
| 2008/0300188 A1 | 12/2008 | Yang et al. | |
| 2009/0092607 A1 | 4/2009 | Gillies et al. | |

FOREIGN PATENT DOCUMENTS

| | | |
|---|---|---|
| JP | 2010531134 A | 9/2010 |
| JP | 2012-107042 A | 6/2012 |
| KR | 10-2009-0122430 A | 11/2009 |
| KR | 10-1235124 B1 | 2/2013 |
| RU | 2370276 C2 | 10/2009 |
| WO | 2005063808 A1 | 7/2005 |

OTHER PUBLICATIONS

Hu, Yu-wen. Efficiency of hemodialysis combined with peritoneal dialysis in patients with chronic renal failure. Zhongguo Manxingbing Yufang Yu Kongzhi. Abstract. vol. 21(3), 338-339 (2013). (Year: 2013).*
Genexine Inc. Study to Evaluate the Efficacy and Safety of GX-E2 in Anemic Patients Diagnosed with Chronic Kidney Disease (CKD)[online]. ClinicalTrials.gov Identifier: NCT02044653. Posted Jan. 24, 2014 [retrieved on Apr. 13, 2021]. Retrieved from clinicaltrials.gov/ct/show/NCT02044653, pp. 1-11. (Year: 2014).*
Taiwanese Intellectual Property Office; Communication dated Oct. 31, 2017 in counterpart application No. 105100659.
Japanese Patent Office; Communication dated Jun. 5, 2018 in counterpart application No. 2017-536578.
Se Jin Im, et al., "Natural Form of Noncytolytic Flexible Human Fc as a Long-Action Carrier of Agonistic Ligand, Erythropoietin", Sep. 2011, pp. 1-13, vol. 6, issue 9, PLoS One, e24574 (13 pages total).
European Patent Office; Communication dated Jun. 26, 2018 in counterpart application No. 16735196.4.
Anonymous, "History of Changes for Study: NCT08044653 Study to Evaluate the Efficacy and Safety of GX-E2 in the Anemic Patients Diagnosed With Chronic Kidney Disease (CKD)", Jan. 22, 2014, XP055484650 (7 pages total).

(Continued)

*Primary Examiner* — Joanne Hama
*Assistant Examiner* — Regina M DeBerry
(74) *Attorney, Agent, or Firm* — Sughrue Mion, PLLC

(57) ABSTRACT

The present invention relates to a method for treating anemia using a long-acting EPO formulation, and more specifically, a method for treating patients with anemia by confirmation of safe, long-acting, and optimal effective dosage and usage in administering a fusion polypeptide which comprises an EPO and an immunoglobulin hybrid Fc to patients with anemia. The method of administering the fusion polypeptide employs an appropriate dosage and usage which not only shows an excellent long-acting property compared to the existing EPO products but also minimizes cardiovascular side effects that may occur due to a rapid increase in hemoglobin level, which is an effect of anemia treatment.

16 Claims, 7 Drawing Sheets
Specification includes a Sequence Listing.

(56) References Cited

OTHER PUBLICATIONS

Hyekyung Han, "Exploration of the Effect and Pharmacokinetics of Intravenous and Subcutaneous GC1113, a Novel Erythropoiesis-Stimulating Agent", Jan. 1, 2008, Korea (South), XP055484670 (100 pages total).

Hyekyung Han, et al., "Pharmacodynamics, Pharmacokinetics, and Tolerability of Intravenous or Subcutaneous GC1113, a Novel Erythropoiesis-Stimulating Agent", Clinical Drug Investigation, Jun. 2014, pp. 373-382, vol. 34, Issue 6.

NCBI, GenBank accession No. ACJ06770.1, dated May 29, 2009.

Xunlong Shi, et al., "Pharmacokinetics and Pharmacodynamics of Recombinant Human EPO-Fc Fusion Protein In Vivo", PloS One, Aug. 2013, e72673, pp. 1-7, vol. 8, Issue 8.

Se Hwan Yang, et al., "A Long-acting Erythropoietin Fused with Noncytolytic Human Fc for the Treatment of Anemia", Archives of Pharmacal Research, 2012, pp. 757-759, vol. 35, No. 5.

International Search Report of PCT/KR2016/000175, dated May 11, 2016. [PCT/ISA/210].

\* cited by examiner

[FIG. 1A]
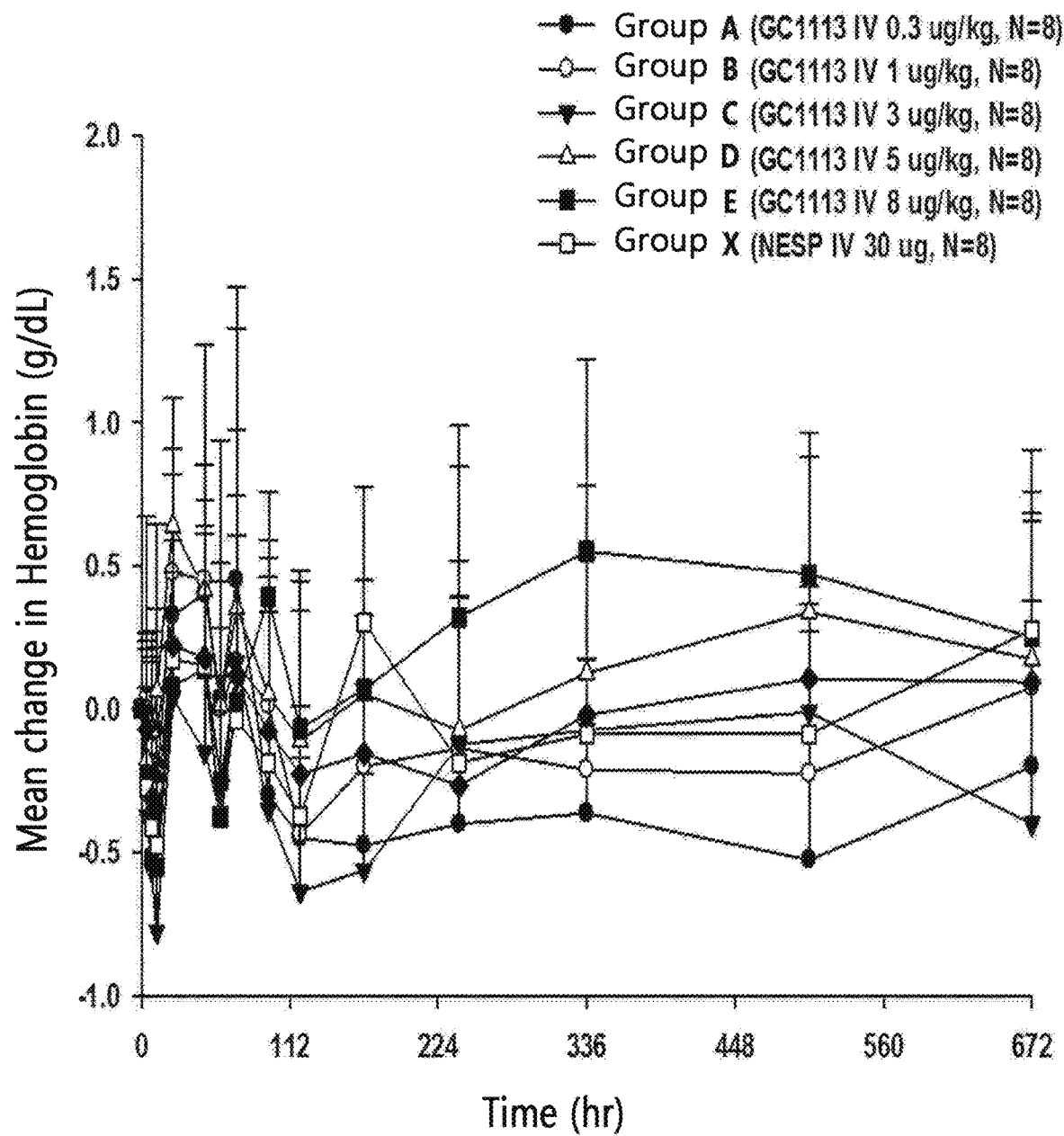

[FIG. 1B]
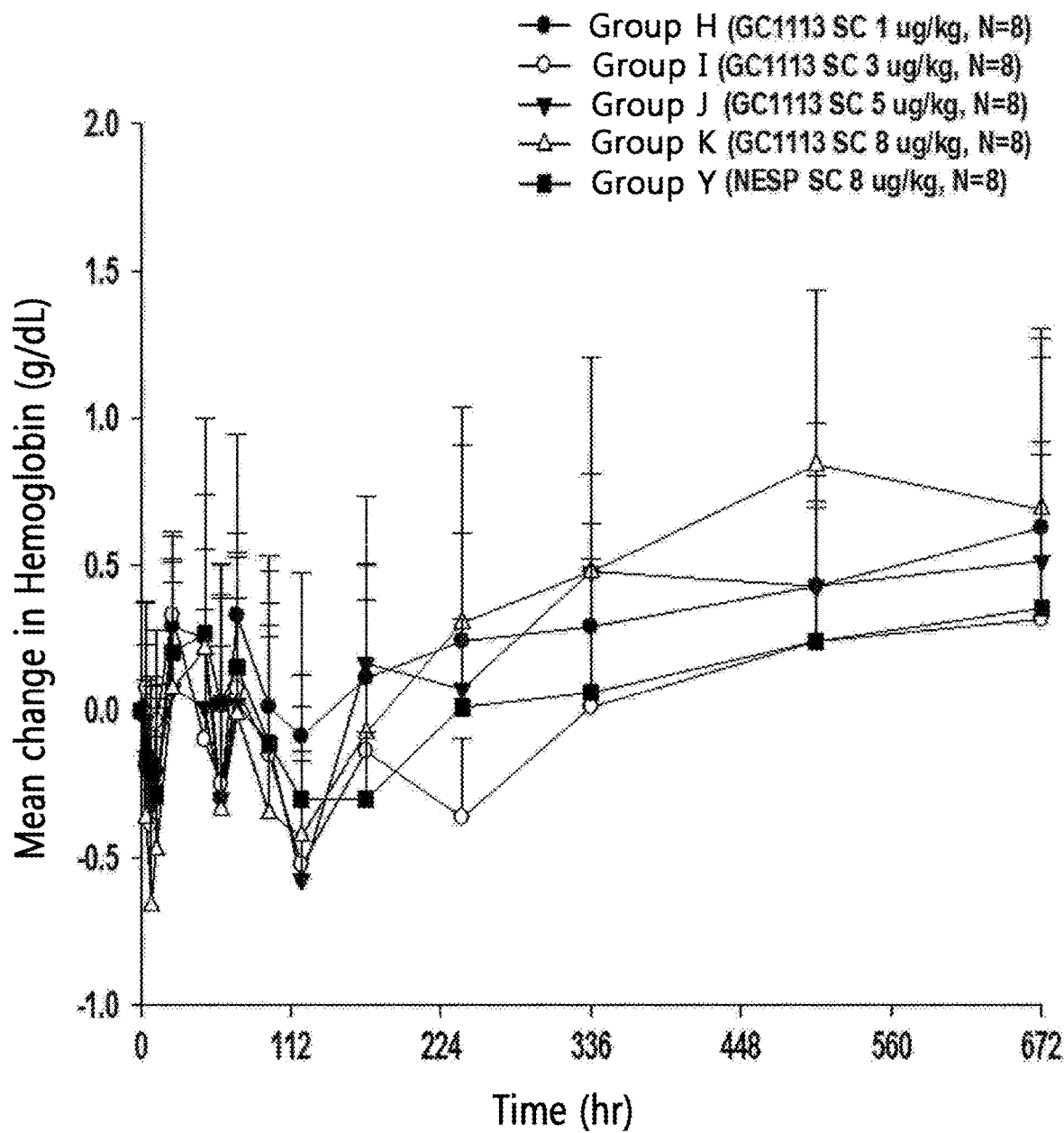

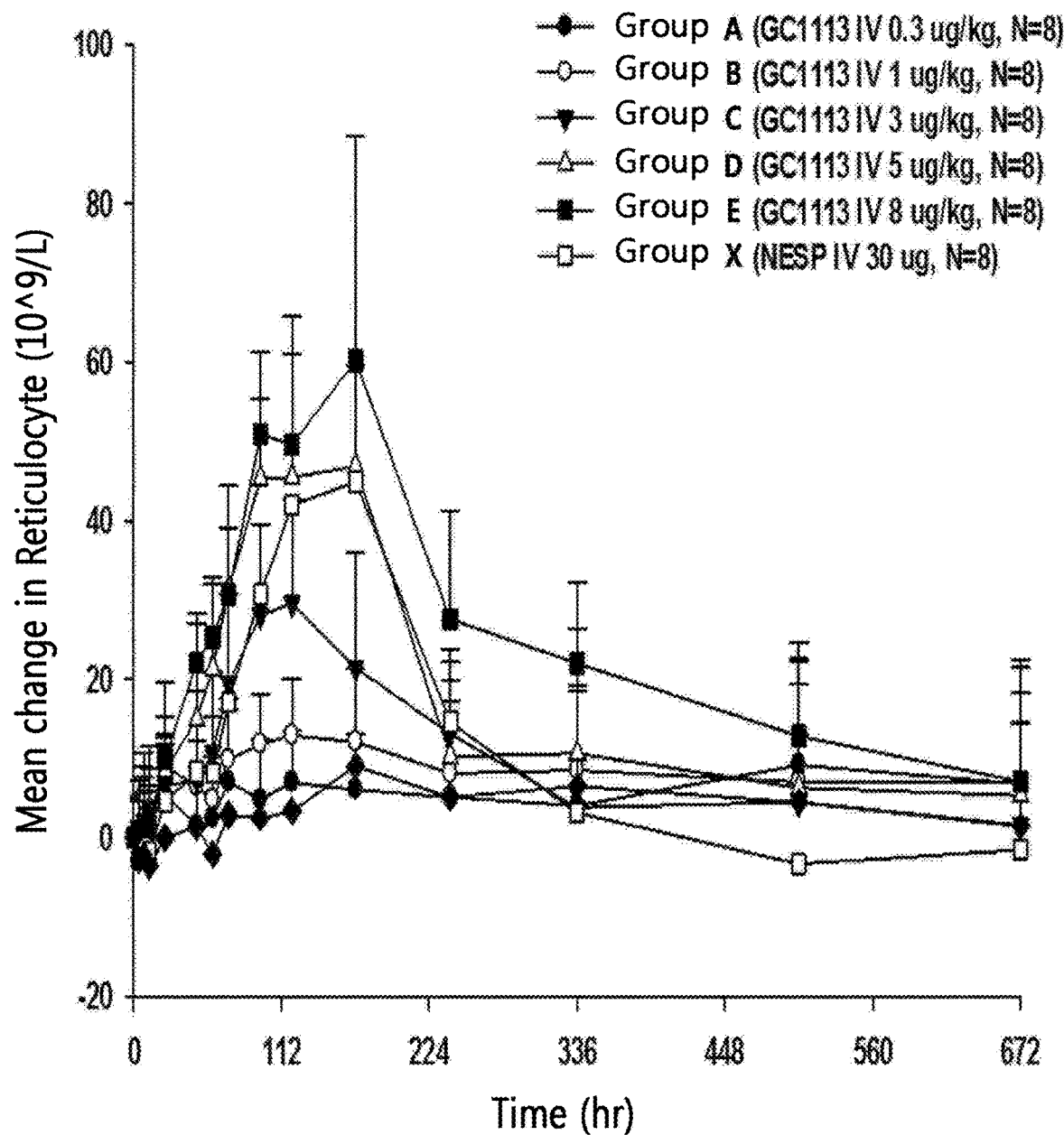
[FIG. 1C]

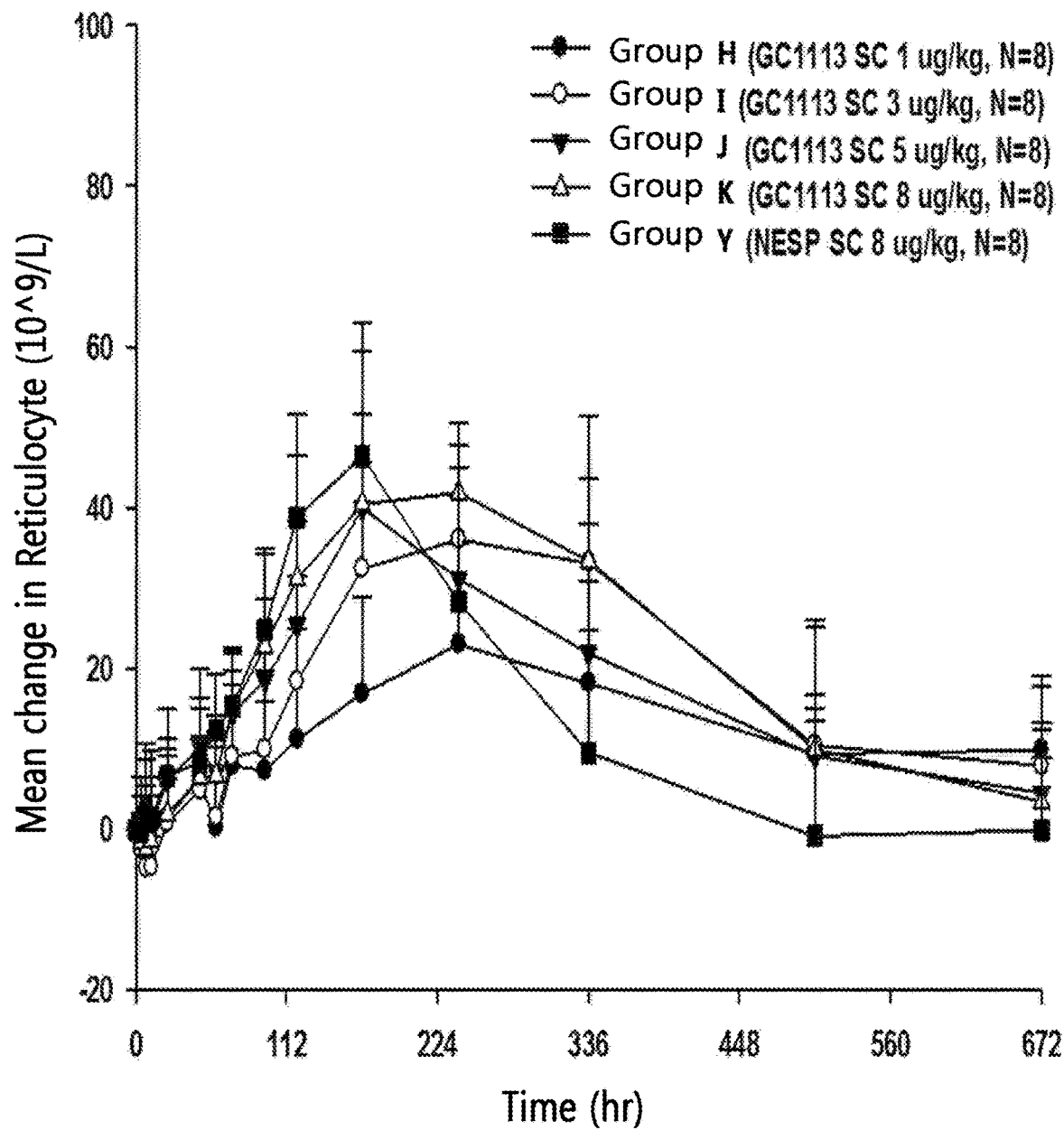
[FIG. 1D]

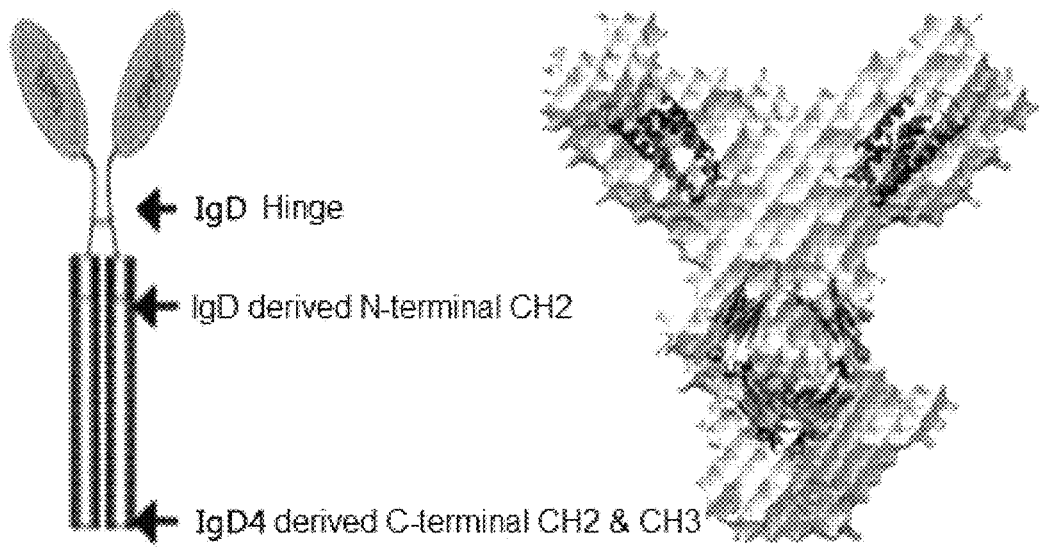

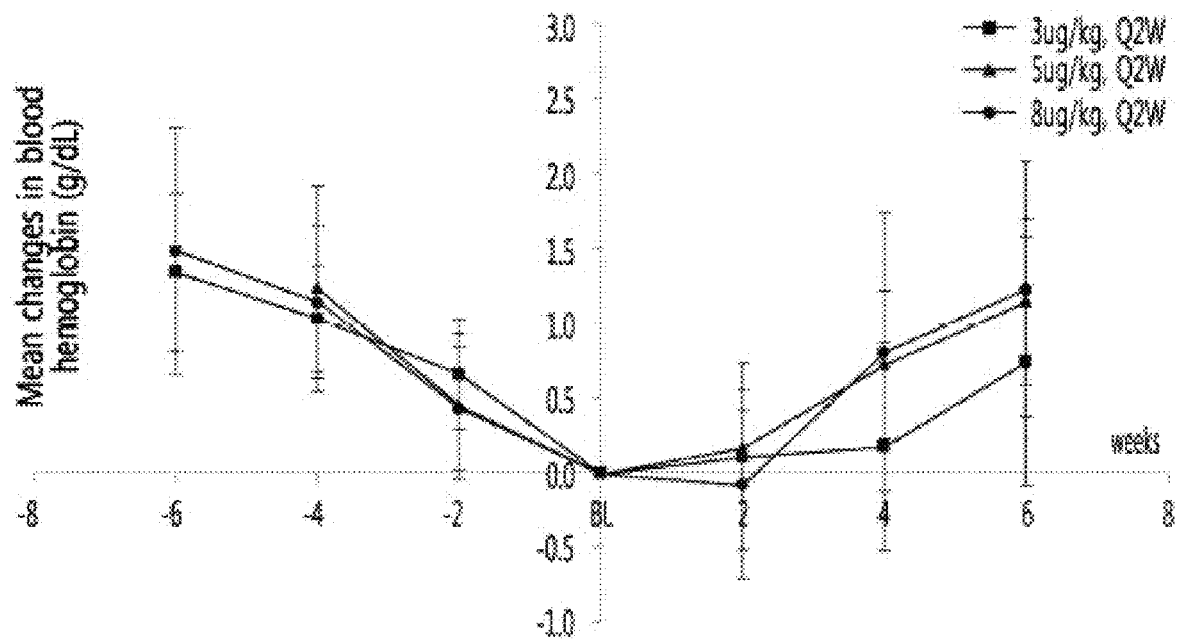

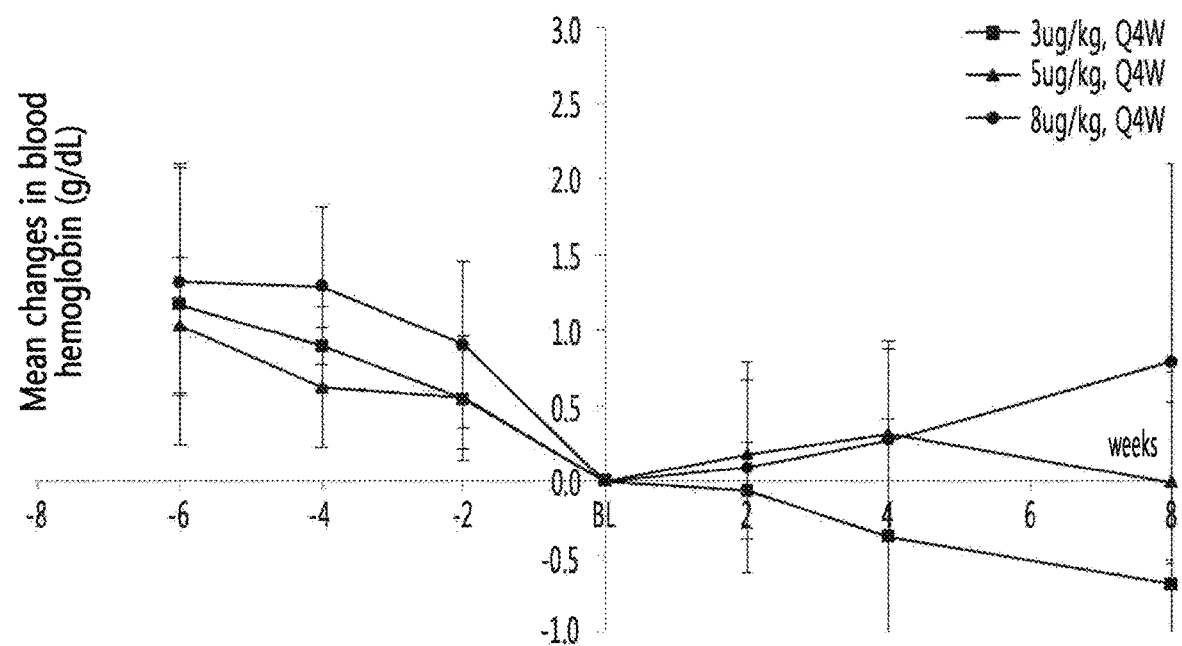
[FIG. 4B]

SEQUENCE LISTING

```
<160> NUMBER OF SEQ ID NOS: 3

<210> SEQ ID NO 1
<211> LENGTH: 166
<212> TYPE: PRT
<213> ORGANISM: Artificial Sequence
<220> FEATURE:
<223> OTHER INFORMATION: Mature Erythropoietin amino acid sequence

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 245
<212> TYPE: PRT
<213> ORGANISM: Artificial Sequence
<220> FEATURE:
<223> OTHER INFORMATION: hyFc polypeptide amino acid sequence

<400> SEQUENCE: 2

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45
```

```
Leu Met Ile Ser Arg Thr Pro Glu Val Thr Cys Val Val Asp Val
 50              55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
                115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
                195                 200                 205

Thr Val Asp Lys Ser Arg Trp Gln Glu Gly Asn Val Phe Ser Cys Ser
210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 3
<211> LENGTH: 411
<212> TYPE: PRT
<213> ORGANISM: Artificial Sequence
<220> FEATURE:
<223> OTHER INFORMATION: EPO-hyFc amino acid sequence

<400> SEQUENCE: 3

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
 50                 55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160
```

-continued

```
Cys Arg Thr Gly Asp Arg Arg Asn Thr Gly Arg Gly Gly Glu Glu Lys
            165                 170                 175
Lys Lys Glu Lys Glu Lys Glu Glu Gln Glu Glu Arg Glu Thr Lys Thr
            180                 185                 190
Pro Glu Cys Pro Ser His Thr Gln Pro Leu Gly Val Phe Leu Phe Pro
            195                 200                 205
Pro Lys Pro Lys Asp Thr Leu Met Ile Ser Arg Thr Pro Glu Val Thr
    210                 215                 220
Cys Val Val Val Asp Val Ser Gln Glu Asp Pro Glu Val Gln Phe Asn
225                 230                 235                 240
Trp Tyr Val Asp Gly Val Glu Val His Asn Ala Lys Thr Lys Pro Arg
                245                 250                 255
Glu Glu Gln Phe Asn Ser Thr Tyr Arg Val Val Ser Val Leu Thr Val
            260                 265                 270
Leu His Gln Asp Trp Leu Asn Gly Lys Glu Tyr Lys Cys Lys Val Ser
            275                 280                 285
Asn Lys Gly Leu Pro Ser Ser Ile Glu Lys Thr Ile Ser Lys Ala Lys
    290                 295                 300
Gly Gln Pro Arg Glu Pro Gln Val Tyr Thr Leu Pro Pro Ser Gln Glu
305                 310                 315                 320
Glu Met Thr Lys Asn Gln Val Ser Leu Thr Cys Leu Val Lys Gly Phe
                325                 330                 335
Tyr Pro Ser Asp Ile Ala Val Glu Trp Glu Ser Asn Gly Gln Pro Glu
            340                 345                 350
Asn Asn Tyr Lys Thr Thr Pro Pro Val Leu Asp Ser Asp Gly Ser Phe
            355                 360                 365
Phe Leu Tyr Ser Arg Leu Thr Val Asp Lys Ser Arg Trp Gln Glu Gly
    370                 375                 380
Asn Val Phe Ser Cys Ser Val Met His Glu Ala Leu His Asn His Tyr
385                 390                 395                 400
Thr Gln Lys Ser Leu Ser Leu Ser Leu Gly Lys
            405                 410
```

METHOD OF TREATING ANEMIA USING LONG-ACTING EPO FORMULATION

CROSS REFERENCE TO RELATED APPLICATIONS

This application is a National Stage of International Application No. PCT/KR2016/000175 filed Jan. 8, 2016, claiming priority based on U.S. Provisional Patent Application No. 62/101,639, filed Jan. 9, 2015, the contents of all of which are incorporated herein by reference in their entirety.

TECHNICAL FIELD

The present invention relates to a method of treating anemia using a long-acting erythropoietin (EPO, hereinafter) formulation. More specifically, the present invention relates to a method of treating anemia including administering a fusion polypeptide, which includes an EPO and an immunoglobulin hybrid Fc, to a patient with anemia, and a method of correcting or maintaining the blood hemoglobin level of a patient with anemia.

BACKGROUND ART

An EPO is a glycoprotein hormone that promotes the production of red blood cells. It is produced by the kidneys according to the in-vivo oxygen concentration and is well known as a factor to control erythropoiesis. Red blood cells are blood cells essential for the transport of oxygen in-vivo. Patients with renal failure may develop a disorder in EPO release and thus affect the erythropoiesis thereby showing symptoms of anemia.

According to the World Health Organization (WHO), anemia is defined as blood hemoglobin concentrations of lower than 13.0 g/dL for adult men and postmenopausal women, or lower than 12.0 g/dL for premenopausal women (World Health Organization. Nutritional Anaemias: Report of a WHO Scientific Group. Geneva, Switzerland: World Health Organization, 1968). Based on the above standards, the blood hemoglobin has been reported to be lower than 10 g/dL in 90% or more of the anemia patients having the glomerular filtration rate (GFR)<25 mL/min to 30 mL/min (the fourth stage of renal failure) (Kazmi W H, Kausz A T, Khan S, et al. Anemia: an early complication of chronic renal insufficiency. Am J Kidney Dis 2001; 38:803).

Anemic conditions can be improved by administering EPO agents to alleviate anemia symptoms. For this purpose, the first generation products of EPO products prepared by genetic recombination, such as EPOGEN® and NEORECORMON® led by Amgen Inc., were released.

However, these first generation products were not convenient because they had to be administered three times a week due to their short half-lives. Accordingly, for the purpose of improving patient convenience, long-acting EPO products, such as ARANESP® and MICERA®, which can be administered once a week, once every two weeks, or once a month, have been released in the 2000s. However, there is still a need for the development of EPO products with longer half-lives for the sake of patient convenience, and there is also a need for the development of bio-friendly and long-acting EPO products prepared without utilizing chemical bindings. Additionally, in developing long-acting EPO agents, it has been highlighted that the risk of cardiovascular-related adverse effects due to a rapid increase or frequent changes in hemoglobin levels should be minimized, in addition to the need for the long-term in-vivo maintenance of their efficacies for improving patient convenience.

The present inventors have developed an EPO-hyFc fusion polypeptide (U.S. Pat. No. 7,867,491, the content of which is incorporated herein by reference), in which the EPO protein and an immunoglobulin hybrid Fc are fused, and it was confirmed that when the EPO-hyFc fusion polypeptide was administered to healthy adults, the in-vivo duration was maintained without showing any serious adverse effect by the drug, similarly to the existing conventional products (Clinical Drug Investigation June 2014, Volume 34, Issue 6, pp 373-382).

However, since the result was based on healthy adults, it was not certain whether the drug will show the same therapeutic effect on patients with anemia. In addition, the result only confirmed the safety of single administration of the drug and it did not reveal anything regarding the essential administration interval of the drug, which is necessary for a long-term administration therapy. Furthermore, since healthy adults have the physiological regulatory activities to maintain homeostasis when the administration of the EPO agent increases the hemoglobin concentration higher than the physiologically normal range, it was not possible to accurately confirm the changes in hemoglobin level, which serves as a pharmacodynamic parameter by the EPO-hyFc. Accordingly, the effect of single administration of the EPO agent could only be predicted by measuring the changes in reticulocytes, which are precursors of erythrocytes, as a leading indicator.

As such, there has been a request for the establishment of a safer and more sustainable method for administering an EPO-hyFc fusion polypeptide with an appropriate effective dose and interval for treating anemia.

DISCLOSURE

Technical Problem

The present inventors have endeavored to develop a safer and more sustainable method for treating anemia. As a result, when the inventors administered a fusion protein including an EPO and an immunoglobulin hybrid Fc to patients with anemia, the inventors have discovered an optimal dose and administration interval of the fusion protein showing a significant effect, which had not been confirmed previously, thereby completing the present invention.

Technical Solution

An object of the present invention is to provide a method of treating anemia by administering a safe and long-acting fusion polypeptide with an effective dose and administration interval, which includes an EPO and an immunoglobulin hybrid Fc.

Another object of the present invention is to provide a method of correcting or maintaining the blood hemoglobin level of a patient with anemia by the above administration.

Advantageous Effects of the Invention

The present invention relates to an optimal administration dose and interval of a fusion polypeptide including an EPO, which shows a gradual increase of hemoglobin levels while showing excellent safety and maintaining in-vivo duration for up to one month, and an immunoglobulin hybrid Fc. The method of administering the fusion polypeptide including an EPO and the immunoglobulin hybrid Fc, utilizing the optimal administration dose and interval, can be effectively used for the treatment of patients with anemia.

BRIEF DESCRIPTION OF THE DRAWINGS

FIGS. 1A to 1D show graphs respectively illustrating the changes in levels of hemoglobin and reticulocytes in healthy adults according to intravenous administration and subcutaneous administration of an EPO-hyFc fusion polypeptide, in which FIG. 1A and FIG. 1C show the result of intravenous administration and FIG. 1B and FIG. 1D show the result of subcutaneous administration.

FIGS. 2A and 2B relate to the EPO-hyFc fusion polypeptide, in which FIG. 2A shows a schematic diagram and a structure of the EPO-hyFc fusion polypeptide, and FIG. 2B shows an amino acid sequence of the EPO-hyFc fusion polypeptide. In FIG. 2B, the italicized part represents the hinge region of IgD, the underlined part represents the CH2 domain of IgD, and the bolded part represents the CH2 and CH3 domains of IgG4.

FIG. 3 shows a constitution of a clinical test designed to confirm the change in hemoglobin level according to each dose after administering the EPO-hyFc fusion polypeptide to a patient with chronic renal-failure and anemia, in which HD represents hemodialysis. PD represents peritoneal dialysis. CRF represents chronic renal failure. Q1W represents administration at 1 week interval, Q2W represents administration at 2 week interval, and Q4W represents administration at 4 week interval, respectively.

FIGS. 4A and 4B show graphs illustrating the range of fluctuation of hemoglobin levels according to dose when the EPO-hyFc fusion polypeptide was administered to a patient with chronic renal-failure anemia, in which BL represents a baseline.

BEST MODE

To achieve the above objects, in an aspect, the present invention provides a method of treating anemia including administering a fusion polypeptide including an EPO and an immunoglobulin hybrid Fc at a dose of from 4 μg/kg to 9 μg/kg at intervals of 2 weeks to 4 weeks.

The present invention has established optimum administration dose and administration interval for a fusion polypeptide including an EPO and an immunoglobulin hybrid Fc, which can correct or maintain the blood hemoglobin level to normal, when administered to a patient with anemia. Accordingly, the administration of the fusion polypeptide to patients with anemia at the established administration dose and administration interval in the present invention can correct or maintain the blood hemoglobin level of the patient to normal range, and ultimately treating anemia. The present invention will be described in detail herein below.

As used herein, the term "erythropoietin (EPO)", which is a glycoprotein hormone, refers to a cytokine involved in erythropoiesis. The EPO may be derived from various species, for example, humans, cynomolgus monkeys, mice, rats, and rabbits, but is not particularly limited thereto as long as it can increase the blood hemoglobin level.

Specifically, the EPO may be consisting of the amino acid sequence of SEQ ID NO: 1, or one having a sequence homology of 70% or greater to the amino acid sequence, specifically 80% or greater, more specifically 90% or greater, much more specifically 95% or greater, even more specifically 98% or greater, and most specifically 99% or greater, although not limited thereto.

It is obvious that amino acid sequences in which part of the sequence is deleted, modified, substituted, or inserted can be also included in the scope of the present invention as long as they are the sequences having a sequence homology to the above sequences and have the same or similar biological activity to the protein of SEQ ID NO: 1.

As used herein, the term "homology" refers to a degree of identity with a given amino acid sequence or a nucleotide sequence, and may be indicated in percentage. As used herein, the homologous sequence having the same or similar activity with the given amino acid sequence or nucleotide sequence may be indicated in terms of "% homology". For example, the % homology may be confirmed using standard software, e.g., BLAST 2.0, for calculating parameters such as score, identity, and similarity, or by comparing sequences via southern hybridization experiments under the strictly defined condition. The appropriate hybridization condition to be defined may be determined by a method known to a skilled person in the art (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology. John Wiley & Sons, Inc., New York).

As used herein, the term "an immunoglobulin Fc fragment" or "an immunoglobulin Fc" refers to a protein, which includes the heavy-chain constant region (CH) of an immunoglobulin, except for the variable regions of the heavy and light chains and the light-chain constant region (CL) of an immunoglobulin. The immunoglobulin Fc region may further include a hinge region, and for the purpose of the present invention, may include the heavy-chain constant region 2 (CH2) and the heavy-chain constant region 3 (CH3) but may or may not include the heavy-chain constant region 1 (CH1).

Additionally, the immunoglobulin Fc fragment of the present invention may be in the form of having native sugar chains or increased or decreased sugar chains compared to the native form, or may be in a deglycosylated form. The increase, decrease, or removal of the immunoglobulin Fc sugar chains may be achieved by conventional methods in the art, such as a chemical method, an enzymatic method, and a genetic engineering method using a microorganism. The removal of sugar chains from Fc fragment results in a significant decrease in binding affinity to the C1q part of the first complement component C1 and a decrease or loss in antibody-dependent cell-mediated cytotoxicity (ADCC) or complement-dependent cytotoxicity (CDC), and thus does not induce unnecessary immune responses in vivo. In this regard, the immunoglobulin Fc fragment in a deglycosylated or aglycosylated form may be more suitable to the object of the present invention as a drug carrier.

As used herein, the term "deglycosylation" refers to the enzymatical removal of sugar moieties from an Fc fragment, and the term "aglycosylation" refers to the production of an unglycosylated Fc fragment in a prokaryote, preferably in *E. coli*.

The immunoglobulin Fc may be any one of Fc regions of IgG1, IgG2, IgG3, or IgG4. Additionally, the immunoglobulin Fc may be one which was modified to prevent the occurrence of FcR binding and/or complement binding. In particular, the hybrid Fc was used as the immunoglobulin Fc in the present invention, and it was designated as "immunoglobulin hybrid F". In the present invention, the term "immunoglobulin hybrid Fc" was used interchangeably with "hyFc".

The immunoglobulin hybrid Fc may be induced from a combination of IgG subclasses or a combination of human IgD and human IgG. For example, the immunoglobulin Fc region may include a hinge region, a CH2 domain, and a CH3 domain in the direction from the N-terminus to the C-terminus. In particular, the hinge region may include a human IgD hinge region. Additionally, the CH2 domain may include the amino acid residues of the human IgD and the IgG4 CH2 domain. Additionally, the CH3 domain may include the amino acid residues of the human IgG4 CH3 domain.

Specifically, the immunoglobulin hybrid Fc may be consisting of the amino sequence of SEQ ID NO: 2, or one having a sequence homology of 70% or greater to the amino acid sequence, specifically 80% or greater, more specifically 90% or greater, much more specifically 95% or greater, even more specifically 98% or greater, and most specifically 99% or greater, although not limited thereto.

It is obvious that amino acid sequences in which part of the sequence is deleted, modified, substituted, or inserted can be also included in the scope of the present invention as long as they are the sequences having a sequence homology to the above sequences and have the same or similar biological activity to the protein of SEQ ID NO:2.

When the immunoglobulin hybrid Fc binds to an EPO protein, it can increase serum half-life of the EPO while not inhibiting its activity.

As used herein, the term "a fusion polypeptide including an EPO protein and an immunoglobulin hybrid Fc" refers to a fusion protein, in which an immunoglobulin Fc is fused to an EPO protein. In the present invention, the term "a fusion polypeptide including an EPO and an immunoglobulin hybrid Fc" was used interchangeably with "an EPO-hyFc fusion polypeptide". Specifically, the fusion polypeptide may be one in which the N-terminus of an immunoglobulin hybrid Fc and the C-terminus of an EPO are bound to each other, but it is not limited thereto. Additionally, the fusion protein may be one in which the immunoglobulin hybrid Fc and the EPO are connected by a linker.

Specifically, the immunoglobulin hybrid Fc may be consisting of the amino sequence of SEQ ID NO: 3, or one having a sequence homology of 70% or greater to the amino acid sequence, specifically 80% or greater, more specifically 90% or greater, much more specifically 95% or greater, even more specifically 98% or greater, and most specifically 99% or greater, although not limited thereto.

It is obvious that amino acid sequences in which part of the sequence is deleted, modified, substituted, or inserted can be also included in the scope of the present invention as long as they are the sequences having a sequence homology to the above sequences and have the same or similar biological activity to the protein of SEQ ID NO:3.

The fusion polypeptide including an EPO and an immunoglobulin hybrid Fc is very safe in vivo because no antibody generation is observed after administration of the fusion polypeptide into patients with anemia, and the fusion polypeptide can maintain its half-life for from 138 hours to 158 hours, which is about 19 times higher than those of the first generation EPO products, which is about 8 hours (Sports Med 2003; 33 (4): 301-315).

In an exemplary embodiment of the present invention, a test plan for confirming the range of efficacy of the EPO-hyFc fusion polypeptide through the changes in hemoglobin levels in patients with chronic renal-failure and anemia by repeated administration of the EPO-hyFc fusion polypeptide was established (FIG. 3). Furthermore, the administration dose and interval of the EPO-hyFc fusion polypeptide, which can be effectively used for treating anemia by reducing the risk of cardiovascular-related adverse effects by preventing a rapid effective reaction while maintaining sustainability, were confirmed (Table 1).

As such, it was confirmed that anemia can be effectively treated by administering the EPO-hyFc fusion polypeptide to patients with anemia at a dose of 4 µg/kg to 9 µg/kg at intervals of 2 weeks to 4 weeks by correcting or maintaining the blood hemoglobin levels to normal level.

As used herein, the term "anemia" refers to a deficiency in the number of erythrocytes and/or hemoglobin levels, which are caused by inappropriate production of functional EPO proteins by the EPO-producing cells of patients, and/or inappropriate release of EPO proteins into systemic circulation system, and/or incompetent response of erythroblasts in the bone marrow to EPO proteins. Patients with anemia symptoms cannot maintain erythrocyte homeostasis. In general, anemia may be caused by deterioration or loss of renal functions (e.g., chronic renal failure), relative EPO deficiency, congestive heart failure, myelosuppressive therapy such as chemotherapy or antiviral therapy (e.g., AZT), non-myelogenous cancer, viral infections such as HIV, autoimmune diseases (e.g., rheumatoid arthritis), liver diseases, multiple organ system failure, etc., but is not limited thereto.

In the present invention, the patients with anemia may be those patients who periodically receive peritoneal dialysis or hemodialysis, but are not limited thereto. In particular, the patients may be humans, but are not limited thereto.

As used herein, the term "treatment" refers to any action to be associated with the improvement or advantageous changes in symptoms of anemia by administering the EPO-hyFc fusion polypeptide according to the present invention or a pharmaceutical composition containing the same. The administration refers to providing a particular material to patients by any appropriate method and the administration route of the EPO-hyFc fusion polypeptide of the present invention may not be limited as long as the fusion polypeptide can arrive at the target tissue. For example, the EPO-hyFc fusion polypeptide of the present invention may be administered intraartricularly, intraperitoneally, intravenously, intramuscularly, subcutaneously, intradermally, orally, topically, intranasally, intrapulmonarily, and intrarectally, and specifically intravenously or subcutaneously.

The method of treating anemia of the present invention may be performed by administering the EPO-hyFc fusion polypeptide a patient with anemia at a dose of from 4 µg/kg to 9 µg/kg at intervals of 2 weeks to 4 weeks.

Specifically, the method of treating anemia may be to administer the EPO-hyFc fusion polypeptide at a dose of from 5 µg/kg to 8 µg/kg, and more specifically, 5 µg/kg or 8 µg/kg. Additionally, the method may be to administer the EPO-hyFc fusion polypeptide at intervals of 2 weeks or 4 weeks. Most specifically, the method may be to administer the EPO-hyFc fusion polypeptide at a dose of 5 µg/kg at intervals of 2 weeks, at a dose of 8 µg/kg at intervals of 2 weeks, at a dose of 5 µg/kg at intervals of 4 weeks, or at a dose of 8 µg/kg at intervals of 4 weeks.

The method of treating anemia may be to correct or maintain the blood hemoglobin level of a patient with anemia to a normal range by administering the EPO-hyFc fusion polypeptide.

As used herein, the term "correction" refers to an action of inducing an abnormal state to become a normal state, and "maintenance" refers to an action of sustaining the normal state. That is, the correction or maintenance of the blood hemoglobin level to a normal range refers to an induction of an abnormal blood hemoglobin level to become normal or sustaining the normal blood hemoglobin level.

Recently, the drug regulatory organizations in each country, including the U.S. FDA, have been recommending that therapeutic agents for treating anemia be carefully administered to be accompanied by careful monitoring, because there is an increased risk of developing cardiovascular-associated adverse effects when there is a rapid increase in hemoglobin levels, and in particular, the organizations have been recommending that EPO agents be administered to patients with severe anemia. According to the Clinical Practice Guideline (2012 KDIGO Clinical Practice Guideline for Anemia in Chronic Kidney Disease, Page 304), the initial administration goal of the EPO agents, which are used for treating patients with renal-failure and anemia, is preferably to achieve an increase of hemoglobin levels to arrive at from 1 g/dL to 2 g/dL during the four weeks after the administration. However, according to the real clinical report, the increase of hemoglobin levels was in the range of from 0.7 g/dL to 2.5 g/dL.

The goal of anemia treatment in patients with renal failure is to maintain the blood hemoglobin level in the range of from 10 g/dL to 12 g/dL. According to reports, when the blood hemoglobin level increases to 13 g/dL or higher, there is an increased level of risk in terms of cardiovascular-associated adverse effects and death, and thus new guidelines have been recently provided to stop the administration of the EPO agents or to adjust the dosage when the blood hemoglobin level increases to 11 g/dL or higher (2011, FDA Drug Safety Communication: Modified dosing recommendations to improve the safe use of Erythropoiesis-Stimulating Agents (ESAs) in chronic kidney disease).

Additionally, according to the treatment guidelines of the U.S. National Kidney Foundation Kidney disease Outcome Quality Initiative (NFK-K/DOQI) in 2007, people having the hemoglobin concentration at 11.0 g/dL or below are recommended to receive therapeutic treatments with the EPO agents, and the target hemoglobin concentration for treatment is in the range of from 11.0 g/dL to 12.0 g/dL and the measurement of hemoglobin concentration at least once a month is recommended (KDOQI clinical practice guidelines and clinical practice recommendations for anemia in chronic kidney disease. Am J Kidney Dis 2006; 47(5 suppl 3): S11-145). According to the KDIGO guidelines in 2012, the patients with stage 5 renal failure are recommended to take EPO agents when the Hb concentration is in the range of from 9.0 g/dL to 10.0 g/dL, and in the case of maintenance therapy, the blood hemoglobin concentration is recommended not to become higher than 11.5 g/dL (Klinger A S, Foley R N, Goldfarb D S, et al. KDOQI US commentary on the 2012 KDIGO clinical practice guideline for anemia in CKD. Am J Kidney Dis 2013).

In the present invention, the correction of anemia may be defined as administering the EPO-hyFc fusion polypeptide to a patient with anemia having the blood hemoglobin level less than that of normal range so that the blood hemoglobin level of the patient can reach a normal level, and the maintenance may be defined as administering the EPO-hyFc fusion polypeptide to a patient with anemia having the blood hemoglobin level within the normal range to continue to maintain at the normal state.

In the correction therapy, the rate of reaching a normal blood hemoglobin level from an abnormal blood hemoglobin level may be very important so as not to cause adverse effects. Specifically, the rate may be one in which the blood hemoglobin level increases from 0.7 g/dL to 2.5 g/dL four weeks after the administration, but is not limited thereto.

In the maintenance therapy, it may be very important to maintain the normal blood hemoglobin level within a small range of variation. Specifically, the maintenance therapy may be to continuously maintain the blood hemoglobin level within the normal range with a small range of variation of from ±1.1 g/dL to 1.3 g/dL (J Am Soc Nephrol, 2009, 20: 479-487), but the range of variation is not limited thereto.

The normal blood hemoglobin level may be, for example, in the range of from 10 g/dL to 12 g/dL, but the range may be appropriate changed according to various factors such as health conditions of a patient, administration method, environment, etc., by one of ordinary skill in the art, and is not particularly limited. Additionally, the correction or maintenance of hemoglobin levels of a patient by controlling the administration interval or dose of the EPO-hyFc fusion polypeptide of the present invention may be also appropriately selected by one of ordinary skill in the art considering the health conditions of the patient and is not particularly limited by one administration dose or interval.

According to an exemplary embodiment of the present invention, when the blood hemoglobin level of an anemia patient, who has a blood hemoglobin level below a randomly selected normal hemoglobin level, reaches a normal range while the patient is being administered with the EPO-hyFc fusion polypeptide at a particular administration dose and interval for the purpose of correction of the hemoglobin level, the administration the EPO-hyFc fusion polypeptide may be performed by changing the dose and interval of the EPO-hyFc fusion polypeptide for the purpose of maintaining the hemoglobin level, and when the hemoglobin level is determined to have been excessively increased, the administration may be temporarily stopped.

In the present invention, the correction therapy may be administering a fusion polypeptide including an EPO and an immunoglobulin hybrid Fc at a dose of from 5 µg/kg to 8 µg/kg, and may be administering the fusion polypeptide at intervals of from 2 weeks to 4 weeks, although not limited thereto. Specifically, the correction therapy may be administering the fusion polypeptide including an EPO and an immunoglobulin hybrid Fc at a dose of 5 µg/kg or 8 µg/kg, and may be administering the fusion polypeptide at intervals of 2 weeks or 4 weeks. More specifically, the correction therapy may be administering the fusion polypeptide including an EPO and an immunoglobulin hybrid Fc at a dose of 5 µg/kg or 8 µg/kg at intervals of 2 weeks, or may be administering the fusion polypeptide including an EPO and an immunoglobulin hybrid Fc at a dose of 8 µg/kg at intervals of 4 weeks.

In the present invention, the maintenance therapy may be administering the fusion polypeptide including an EPO and an immunoglobulin hybrid Fc at a dose of from 5 µg/kg to 8 µg/kg, and may be administering the fusion polypeptide at intervals of 4 weeks, although not limited thereto. Specifically, the maintenance therapy may be administering the fusion polypeptide including an EPO and an immunoglobulin hybrid Fc at a dose of 5 µg/kg or 8 µg/kg. More specifically, the maintenance therapy may be administering the fusion polypeptide including an EPO and an immunoglobulin hybrid Fc at a dose of 5 µg/kg or 8 µg/kg at intervals of 4 weeks.

Additionally, specifically, the method of treating anemia may include: a) correcting by administering the fusion polypeptide, which includes an EPO and an immunoglobulin hybrid Fc, to an anemia patient with a blood hemoglobin level below normal range, at a dose of 5 µg/kg or 8 µg/kg at intervals of 2 weeks; or administering the fusion polypeptide at a dose of 8 µg/kg at intervals of 4 weeks; and b) maintaining by administering the fusion polypeptide, which includes an EPO and an immunoglobulin hybrid Fc, to the patient with anemia having a blood hemoglobin level corrected to normal range through step a), at a dose of 5 µg/kg or 8 µg/kg at intervals of 4 weeks.

In an exemplary embodiment of the present invention, the EPO-hyFc fusion polypeptide of the present invention was repeatedly administered to patients with renal failure at a dose of 3 µg/kg, 5 µg/kg, or 8 µg/kg at intervals of 2 weeks, and the blood hemoglobin levels were continuously monitored (FIG. 4A and Table 1).

As a result, when the EPO-hyFc fusion polypeptide was administered at a dose of 3 µg/kg, the hemoglobin level at the time point of 6 weeks after the administration increased by 0.74 g/dL to reach 9.50 g/dL, which is slightly lower than that of the normal range. In contrast, when the EPO-hyFc fusion polypeptide was administered at a dose of 5 µg/kg, the hemoglobin level increased to 9.74 g/dL, which is an increase of 1.14 g/dL; and when administered at a dose of 8 µg/kg, the hemoglobin level increased to 10.13 g/dL which is an increase of 1.23 g/dL; and thus it was confirmed that when the EPO-hyFc fusion polypeptide was administered at a dose of 5 µg/kg or 8 µg/kg at intervals of 2 weeks, the hemoglobin levels were corrected to be close to the normal level.

From the foregoing results, it was confirmed that when the EPO-hyFc fusion polypeptide of the present invention is to be administered to patients with anemia at intervals of 2 weeks, it is appropriate to perform the administration at a dose of 5 µg/kg or 8 µg/kg, for the correction of hemoglobin levels.

In another exemplary embodiment of the present invention, the EPO-hyFc fusion polypeptide of the present invention was repeatedly administered to patients with renal failure at a dose of 3 µg/kg, 5 µg/kg, or 8 µg/kg at intervals of 4 weeks, and the blood hemoglobin levels were continuously monitored (FIG. 4B and Table 2).

As a result, when the EPO-hyFc fusion polypeptide was administered at a dose of 3 µg/kg, the hemoglobin level at the time point of 8 weeks after the administration decreased by 0.74 g/dL, thus confirming that the symptoms become worsened without any therapeutic effect, contrary to the expectation. In contrast, when the EPO-hyFc fusion polypeptide was administered at a dose of 5 µg/kg, the hemoglobin level decreased by 0.01 g/dL to reach 9.23 g/dL, thus confirming the hemoglobin level before the administration was maintained. Furthermore, when the EPO-hyFc fusion polypeptide was administered at a dose of 8 µg/kg, the hemoglobin level increased by 0.79 g/dL to reach 10.17 g/dL, thus confirming that the hemoglobin level was corrected or maintained to normal level.

From the foregoing results, it was confirmed that when the EPO-hyFc fusion polypeptide of the present invention is to be administered to patients with anemia at intervals of 4 weeks, it is appropriate to perform the administration at a dose of 5 µg/kg for the maintenance of the hemoglobin level, and at a dose of 5 µg/kg or 8 µg/kg, for the correction or maintenance of hemoglobin levels.

In still another exemplary embodiment of the present invention, a method of correcting or maintaining the blood hemoglobin level in a patient with anemia to a concentration of 10 g/dL to 12 g/dL, including administering the fusion polypeptide, which includes an erythropoietin (EPO) and an immunoglobulin hybrid Fc, at a dose of from 4 µg/kg to 9 µg/kg at intervals of 2 weeks to 4 weeks.

The patient with anemia, a fusion polypeptide, and administration are the same as described above.

Specifically, the correction may be administering the fusion polypeptide, which includes an EPO and an immunoglobulin hybrid Fc, at a dose of 5 µg/kg or 8 µg/kg at intervals of 2 weeks; or administering the fusion polypeptide, which includes an EPO and an immunoglobulin hybrid Fc, at a dose of 8 µg/kg at intervals of 4 weeks; and the maintenance may be administering the fusion polypeptide, which includes an EPO and an immunoglobulin hybrid Fc, at a dose of 5 µg/kg or 8 µg/kg at intervals of 4 weeks.

DETAILED DESCRIPTION OF THE INVENTION

Hereinafter, the present invention will be described in more detail with reference to the following Examples. However, these Examples are for illustrative purposes only, and the invention is not intended to be limited by these Examples.

<Example 1> Method of Repeated Administration of an EPO-hyFc Fusion Polypeptide to Patients with Renal-Failure and Anemia 1-1) Preparation of an EPO-hyFc Fusion Polypeptide An EPO-hyFc fusion polypeptide was prepared in the same manner as disclosed in <Example 3> and <Example 4> of U.S. Pat. No. 7,867,491, a previous patent by the present inventors (FIG. 2A). The entire sequence of the EPO-hyFc fusion polypeptide (SEQ ID NO: 3) is shown in FIG. 2B.

1-2) Method of Single Administration

For the confirmation of pharmacodynamic and pharmacokinetic responses of the EPO-hyFc fusion polypeptide prepared above, the EPO-hyFc fusion polypeptide was administered to healthy male adults. The administration was performed once intravenously at respective doses (0.3 µg/kg, 1 µg/kg, 3 µg/kg, 5 µg/kg, or 8 µg/kg) and once subcutaneously at respective doses (1 µg/kg, 3 µg/kg, 5 µg/kg, or 8 µg/kg), and the hemoglobin levels were evaluated (FIGS. 1A and 1B).

As a result, the intravenous and subcutaneous administrations of the EPO-hyFc fusion polypeptide were shown to be stable in all the tested doses. In the case of the intravenous administration, the in-vivo exposure increased along with the increase of the dose. In the case of Cmax with dose calibration, there was no difference in dose, however, in the case of $AUC_{last}$ with dose calibration, there was a significant difference in the in-vivo exposure according to the increase in dose (P-value<0.001). In the case of Cmax, in which the group administered subcutaneously with GC1113 was calibrated with the administration dose, there was no difference according to the dose, however, in the case of $AUC_{last}$ with dose calibration, there was a significant difference from the statistical point of view according to the dose (P-value=0.016). The comparison of pharmacodynamic/pharmacokinetic correlation revealed that there was a correlation in amount between $C_{max}$, $AUC_{last}$ and baseline calibrated Emax, AUEC, and in the case of subcutaneous administration, there was no simple correlation observed between Cmax, $AUC_{last}$ and baseline calibrated $E_{max}$, AUEC (p-value>0.05).

Antibody generation after the administration was not observed, and the group with intravenous administration (IV) of GC1113 at a dose of 1 µg/kg and the group with intravenous administration (IV) of 30 µg NESP® showed similar levels of in-vivo exposure. Upon counting the reticulocytes, which serve as a pharmacodynamic parameter, the group with IV administration at a dose of from 3 µg/kg to 5 µg/kg and the group by IV administration with 30 µg NESP® showed similar features (FIGS. 1C and 1D). In the case of subcutaneous administration, the feature of change in reticulocytes according to time was different from the group administered with 30 μg NESP®. Upon determination based on the reticulocyte-time profile and the changes in value of AUEC per cumulative time zone, it was confirmed that the maximum effect of the increase of reticulocytes in the low-dose groups (1 μg/kg and 3 μg/kg) appeared to be lower and later than the group administered with 30 μg NESP®, whereas the maximum effect of the increase of reticulocytes in the high-dose group (5 μg/kg and 8 μg/kg) was shown to be similar to that of NESP® and be more long-acting.

1-3) Method of Repeated Administration

For the confirmation of the changes in hemoglobin levels in patients with chronic renal-failure and anemia by the EPO-hyFc fusion polypeptide prepared above and the subsequent effect on the treatment of anemia, the fusion polypeptide was administered to patients with chronic renal-failure and anemia at the dose and interval described in FIG. 3.

In Part A, the patients with renal failure (10 patients/group according to the respective dose and administration interval) routinely receiving dialysis were administered with the respective doses (3 μg/kg, 5 μg/kg, or 8 μg/kg) at intervals of 2 weeks or 4 weeks, and the changes in hemoglobin level compared to that before the administration were measured, and the groups with the two highest results were selected and compared with that of the active control group in the study of Part B.

In the case of patients who had been administered with the existing EPO agents participated in the study after going through with a wash-out period. The wash-out period was given for a period of at least 8 weeks. However, when the patients who had already undergone the wash-out period for at least 4 weeks and their tested hemoglobin levels, after measurement of the changes in hemoglobin levels for at least 3 times, were shown to be lower than 10 g/dL, they were recruited even though the assigned wash-out period of at least 8 weeks had not been lapsed.

1-4) Method of Administration for Patients Receiving Peritoneal Dialysis

For investigation of the changes in hemoglobin amount in the body of the patients who routinely receive peritoneal dialysis, clinical studies were performed as follows.

The patients with renal failure (10 patients/group according to the respective dose and administration interval) routinely receiving peritoneal dialysis were administered with the potentially-selected respective doses (3 μg/kg, 5 μg/kg, or 8 μg/kg) subcutaneously 3 times (day 1, day 15, and day 29) or two times (day 1 and day 29) at intervals of 2 weeks or 4 weeks, and the change in hemoglobin level was examined on the $6^{th}$ week or the $8^{th}$ week after the administration and compared to that before the administration. Then, the in-vivo duration and efficacy of the EPO-hyFc fusion polypeptide were evaluated based on the changes in the hemoglobin levels in the body.

In the case of Part A regarding the patients with renal failure requiring peritoneal dialysis, the patients were scheduled to be visited a total of 6 times, and blood samples were collected from the patients per each visit from the $1^{th}$ visit to the $5^{th}$ visit for the evaluation of the effect of hemoglobin increase, and the evaluations on blood loss or necessity of transfusion were conducted per each visit.

Then, for the confirmation of the effect of the in-vivo duration by the repeated administration of EPO-hyFc fusion polypeptide according to its dose on the changes in hemoglobin levels in humans, the two doses selected through Part A were administered subcutaneously to patients with renal failure who were receiving peritoneal dialysis (25 patients/group), and the change in hemoglobin level 12 weeks after the administration was examined compared to that of before the administration.

In the case of Part B, the patients were scheduled to be visited a total of 10 times, and the visits for administrations were performed at intervals of 2 weeks between the $2^{nd}$ visit to the $8^{th}$ visit. Blood samples were collected from the patients per each visit from the $1^{st}$ visit to the $9^{th}$ visit for the evaluation of the effect of hemoglobin increase, and the evaluations on blood loss or necessity of transfusion were conducted per each visit.

1-5) Method of Administration for Patient Groups Receiving Hemodialysis

For confirmation of the changes in hemoglobin levels in the body of the patients who periodically receive hemodialysis and the therapeutic effect for treating anemia by administering the fusion polypeptide, clinical studies were performed as follows.

For confirmation of the effect of the in-vivo duration of the EPO-hyFc fusion polypeptide according to repeated administration for respective doses in humans, each of the doses (5 μg/kg and 8 μg/kg) potentially-selected through the peritoneal dialysis Part A was administered via intravenous (IV) route 13 times (day 1, day 8, day 15, day 22, day 29, day 36, day 43, day 50, day 57, day 64, day 71, day 78, and day 85) or 7 times (day 1, day 15, day 29, day 43, day 57, day 71, and day 85) at intervals of a week or 2 weeks, and the change in hemoglobin level 12 weeks after the administration was examined on the $13^{th}$ or the $14^{th}$ week and compared to that of before the administration. Then, the in-vivo duration and efficacy of the EPO-hyFc fusion polypeptide were evaluated based on the changes in the hemoglobin levels in the body.

In the case of Part B, the patients were scheduled to be visited a total of 16 times (the patients to be administered at intervals of 1 week) or 10 times (the patients to be administered at intervals of 2 weeks), and the visits for administrations were performed at intervals of 1 week or 2 weeks between the $2^{nd}$ visit to the $14^{th}$ visit. Blood samples were collected from the patients per each visit from the $1^{st}$ visit to the $15^{th}$ visit for the evaluation of the effect of hemoglobin increase, and the evaluation on blood loss or necessity of transfusion were conducted per each visit.

<Example 2> Change in Hemoglobin Levels of Patients with Chronic Renal-Failure and Anemia by Repeated Administration of EPO-hyFc The EPO-hyFc fusion polypeptide was repeatedly administered according to each of the administration methods described in <Example 1>, and the hemoglobin count in each of the blood samples of patients was examined using an automatic hematology analyzer, and thereby the changes in the hemoglobin levels according to the administration of the fusion polypeptide was confirmed. As a result, the changes in the hemoglobin levels were observed as shown in Tables 1 and 2 below.

TABLE 1

| Dose/Interval | | Baseline (Day 1) | Week 2 (Day 15) | Week 4 (Day 29) | Week 6 (Day 43) | P-value[1] |
|---|---|---|---|---|---|---|
| 3 μg/kg, Q2W | Hb | 8.75 ± 0.94 | 8.86 ± 1.47 | 8.93 ± 1.34 | 9.50 ± 1.61 | 0.1078 |
| | Change | 0 | 0.11 ± 0.63 | 0.18 ± 0.72 | 0.74 ± 0.92 | — |
| 5 μg/kg, Q2W | Hb | 8.60 ± 0.98 | 8.76 ± 1.11 | 9.32 ± 0.89 | 9.74 ± 1.27 | 0.0078 |
| | Change | 0 | 0.17 ± 0.26 | 0.72 ± 0.55 | 1.14 ± 0.66 | — |
| 8 μg/kg, Q2W | Hb | 8.91 ± 0.87 | 8.83 ± 0.96 | 9.71 ± 0.82 | 10.13 ± 1.18 | 0.0313 |
| | Change | 0 | −0.08 ± 0.63 | 0.81 ± 0.95 | 1.23 ± 0.97 | — |

Experimental Group: EPO-hyFc

[1] Statistical significance test was done by Wilcoxon signed rank test

The results were interpreted considering that the recommended changes in hemoglobin levels in the blood 4 weeks after the administration according to the Clinical Practice Guideline is between 1 g/dL and 2 g/dL and that the changes according to the real clinical report is between 0.7 g/dL and 2.5 g/dL.

In particular, in the case of correction therapy, the blood hemoglobin level was aimed at reaching the normal range of from 10 g/dL and 12 g/dL based on the hemoglobin level at 12 weeks after the administration, and the data analysis was performed based on the same.

In the case of the group administered 3 times with the EPO-hyFc fusion polypeptide at a dose of 3 μg/kg at intervals of 2 weeks, the result in the final analysis of the changes in hemoglobin levels 6 weeks after the administration revealed an increase of the hemoglobin level by an average of 0.74 g/dL to reach 9.50 g/dL, which is lower than the normal hemoglobin level. However, the group administered with the EPO-hyFc fusion polypeptide at a dose of 5 μg/kg at intervals of 2 weeks during the same period showed an average increase of 1.14 g/dL, and the group administered with the EPO-hyFc fusion polypeptide at a dose of 8 μg/kg at intervals of 2 weeks showed an average increase of 1.23 g/dL. From the foregoing results, it was confirmed that the administration of the EPO-hyFc fusion polypeptide to patients with chronic renal-failure and anemia can cause an increase the hemoglobin level in a dose-dependent manner, and in particular, the hemoglobin level can be restored to the normal range when the patients are administered with of the EPO-hyFc fusion polypeptide at doses of 5 μg/kg and 8 μg/kg, respectively.

These results indicate that the administration at doses of 5 μg/kg and 8 μg/kg at intervals of 2 weeks can treat anemia without any rapid change in hemoglobin levels. The patients who had been administered with the existing EPO agents showed a decrease of hemoglobin levels to below 9 g/dL after going through with a wash-out period for 8 weeks. However, after the administration of the EPO-hyFc fusion polypeptide 3 times at doses of 5 μg/kg and 8 μg/kg at intervals of 2 weeks, the hemoglobin levels of the patients were restored to the levels before the wash-out period (FIG. 4A). Based on these results, one of ordinary skill in the art can select doses and administration methods with an appropriate rate of change according to the hemoglobin levels and circumstances taking into consideration of the range of variation for each dose.

TABLE 2

| Dose/Interval | | Baseline (Day 1) | Week 2 (Day 15) | Week 4 (Day 29) | Week 8 (Day 57) | P-value[1] |
|---|---|---|---|---|---|---|
| 3 μg/kg, Q4W | Hb | 9.39 ± 0.5 | 9.33 ± 0.71 | 9.03 ± 1.03 | 8.71 ± 1.56 | 0.2344 |
| | Change | 0 | −0.06 ± 0.32 | −0.37?0.80 | −0.68 ± 1.42 | — |
| 5 μg/kg, Q4W | Hb | 9.24 ± 0.64 | 9.42 ± 0.85 | 9.55 ± 0.76 | 9.23 ± 0.96 | 0.5381 |
| | Change | 0 | 0.18?0.49 | 0.31 ± 0.57 | −0.01?0.54 | — |
| 8 μg/kg, Q4W | Hb | 9.38 ± 0.46 | 9.47 ± 0.86 | 9.65 ± 0.83 | 10.17 ± 1.27 | 0.1514 |
| | Change | 0 | 0.09 ± 0.69 | 0.27?0.70 | 0.79 ± 1.31 | — |

Experimental Group: EPO-hyFc

[1] Statistical significance test was done by Wilcoxon signed rank test

Then, as a result of final analysis of changes in hemoglobin levels, the group administered 2 times at a dose of 3 μg/kg at intervals of 4 weeks showed an average decrease of hemoglobin level by 0.68 g/dL: the group administered 2 times at a dose of 5 μg/kg at intervals of 4 weeks showed an average decrease of hemoglobin level by 0.01 g/dL; and the group administered 2 times at a dose of 8 μg/kg at intervals of 4 weeks showed an average increase of hemoglobin level by 0.79 g/dL. In particular, the administration at a dose of 5 μg/kg maintained the hemoglobin level at 9.23 g/dL, which is similar to that of before the administration, and the administration at a dose of 8 μg/kg increased the hemoglobin level to 10.17 g/dL.

The above patients steadily showed a decrease in hemoglobin levels while going through a 8-week wash-out period, however, when they were administered 2 times with the EPO-hyFc fusion polypeptide at intervals of 4 weeks, the pattern of decrease was altered into a pattern of maintenance (at a dose of 5 μg/kg) or a pattern of increase (at a dose of 8 μg/kg) (FIG. 4B). That is, the rapid decrease rate of the hemoglobin level shown during the wash-out period was ameliorated thus showing a slow slope or converted into an opposite pattern.

From the foregoing, it was confirmed that the administration of the EPO-hyFc fusion polypeptide to patients with chronic renal-failure and anemia 2 times for a period of 4 weeks (administration of 2 times at intervals of 4 weeks) had an effect on the hemoglobin levels in a dose-dependent manner. Additionally, it was confirmed that the increase of the hemoglobin level was not rapid but was rather slow or maintained, over the hemoglobin levels in the entire administration doses.

These results suggest that the control of administration doses and interval of the EPO-hyFc fusion polypeptide may be used as a method for correcting the hemoglobin levels in patients with anemia having hemoglobin levels lower than the target hemoglobin level (e.g., 11 g/dL), or may be used as a method for maintaining the hemoglobin levels in patients with anemia who have already achieved the target hemoglobin levels. That is, in the case of the administration at intervals of 4 weeks, the administration method may be used either as a method for correction or a method for maintenance, according to the selection of doses.

<Example 3> Confirmation of In-Vivo Safety by Repeated Administration of EPO-hyFc After the repeated administration of the EPO-hyFc fusion polypeptide according to the administration method as described in <Example 1>, the safety of the repeated administration of the EPO-hyFc was confirmed based on the clinical syndromes, symptoms, etc., complained by patients. As a result, the frequency of adverse reactions was confirmed as shown in Table 3 below.

TABLE 3

| System Organ Class | Total (60 Patients) Patients (%), [No. of Cases] |
|---|---|
| Blood and lymphatic system disorders | 4 (6.67) [4] |
| Anemia | 4 (6.67) [4] |
| Cardiac disorders | 3 (5.00) [4] |
| Arrhythmia | 1 (1.67) [1] |
| Arteriosclerosis coronary artery | 1 (1.67) [1] |
| Coronary artery disease | 1 (1.67) [1] |
| Palpitations | 1 (1.67) [1] |
| Eye disorders | 2 (3.33) [2] |
| Cataract | 1 (1.67) [1] |
| Diabetic retinopathy | 1 (1.67) [1] |
| Gastrointestinal disorders | 7 (11.67) [8] |
| Abdominal pain | 1 (1.67) [1] |
| Constipation | 2 (3.33) [2] |
| Dyspepsia | 2 (3.33) [2] |
| Gastrointestinal disorder | 1 (1.67) [1] |
| Large intestine polyp | 1 (1.67) [1] |
| Nausea | 1 (1.67) [1] |
| Gastro-intestinal system disorders | 1 (1.67) [1] |
| Gastro-intestinal system disorders | 1 (1.67) [1] |
| General disorders and administration site conditions | 9 (15.00) [11] |
| Asthenia | 2 (3.33) [2] |
| Device damage | 1 (1.67) [1] |
| Fatigue | 2 (3.33) [2] |
| Mass | 1 (1.67) [1] |
| Oedema | 1 (1.67) [1] |
| Oedema peripheral | 2 (3.33) [2] |
| Pyrexia | 2 (3.33) [2] |
| Infections and infestations | 11 (18.33) [12] |

TABLE 3-continued

| System Organ Class | Total (60 Patients) Patients (%), [No. of Cases] |
|---|---|
| Device related infection | 1 (1.67) [1] |
| Lymph node tuberculosis | 1 (1.67) [1] |
| Nasopharyngitis | 4 (6.67) [4] |
| Peritonitis | 6 (10.00) [6] |
| Injury, poisoning, and procedural complications | 1 (1.67) [1] |
| Corneal abrasion | 1 (1.67) [1] |
| Investigations | 3 (5.00) [3] |
| Alanine aminotransferase increased | 1 (1.67) [1] |
| Intraocular pressure increased | 1 (1.67) [1] |
| Liver function test abnormal | 1 (1.67) [1] |
| Metabolism and nutrition disorders | 2 (3.33) [3] |
| Hypercalcaemia | 1 (1.67) [1] |
| Hyperglycaemia | 1 (1.67) [1] |
| Hypoglycaemia | 1 (1.67) [1] |
| Musculoskeletal and connective tissue disorders | 5 (8.33) [5] |
| Ankle fracture | 1 (1.67) [1] |
| Arthralgia | 1 (1.67) [1] |
| Back pain | 1 (1.67) [1] |
| Myalgia | 1 (1.67) [1] |
| Plantar fasciitis | 1 (1.67) [1] |
| Nervous system disorders | 6 (10.00) [6] |
| Dizziness | 1 (1.67) [1] |
| Headache | 4 (6.67) [4] |
| VIIth nerve paralysis | 1 (1.67) [1] |
| Psychiatric disorders | 2 (3.33) [2] |
| Anxiety | 2 (3.33) [2] |
| Respiratory, thoracic, and mediastinal disorders | 9 (15.00) [12] |
| Cough | 4 (6.67) [4] |
| Dyspnoea | 1 (1.67) [1] |
| Oropharyngeal pain | 2 (3.33) [2] |
| Orthopnoea | 1 (1.67) [1] |
| Pleural effusion | 2 (3.33) [2] |
| Pulmonary oedema | 1 (1.67) [1] |
| Rhinorrhoea | 1 (1.67) [1] |
| Skin and subcutaneous tissue disorders | 1 (1.67) [3] |
| Papule | 1 (1.67) [1] |
| Pruritus | 1 (1.67) [1] |
| Seborrhoeic dermatitis | 1 (1.67) [1] |
| Vascular disorders | 4 (6.67) [5] |
| Epistaxis | 1 (1.67) [1] |
| Hypertension | 3 (5.00) [3] |
| Orthostatic hypotension | 1 (1.67) [1] |

As a result of evaluation of all adverse reactions according to Preferred Term (PT) of MedDRA, which is a classification system on adverse effects of pharmaceutical drugs, the adverse reactions with the most frequent occurrence were peritonitis (6 patients, 10.00%), cough (4 patients, 6.67%), anemia (4 patients, 6.67%), nasopharyngitis (4 patients, 6.67%), and headache (4 patients, 6.67%), in this order.

No additional adverse drug reaction (ADR), which was determined to be correlated with the EPO-hyFc administration, was observed other than those described above. Additionally, no findings with clinical significance, regarding physical examination or vital signs as well as in-vitro tests predicted to be correlated with administration dose or administration intervals, was found.

Considering that patients with chronic renal failure belong to a patient group with poor health conditions and that no adverse drug reaction, which is suspected to be correlated with the EPO-hyFc administration, was reported, it was determined that no particular attention is necessary for safety purpose in administering the EPO-hyFc administration. Additionally, based on the observations on the frequency and severity of adverse reactions or serious adverse reactions, in-vitro examination findings, regarding physical examination findings and vital signs of the EPO-hyFc administration, it was concluded that the doses or administration interval of the administered EPO-hyFc did not affect the safety of the administration.

From the foregoing results, it was confirmed that the EPO-hyFc has a long half-life compared to NESP®, the existing long-acting EPO product and does not shown any adverse reaction, thus showing its safety. That is, when the EPO-hyFc fusion polypeptide is administered to patients with anemia at a dose of from 5 μg/kg to 8 μg/kg at intervals of from 2 weeks to 4 weeks, it can provide an increased level of safety compared to that of the existing long-acting EPO products and can be also effectively used as a long-acting therapeutic agent.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. A method of treating anemia in a patient with anemia, comprising administering a fusion polypeptide to the patient at a dose of from 5 µg/kg to 8 µg/kg at an interval of from 2 weeks to 4 weeks, wherein the fusion polypeptide comprises an erythropoietin (EPO) and an immunoglobulin hybrid Fc, and
wherein the fusion polypeptide consists of the amino acid sequence of SEQ ID NO: 3,
wherein anemia is due to renal failure.

2. The method of claim 1, wherein the dose is 5 µg/kg or 8 µg/kg.

3. The method of claim 1, wherein the interval is 2 weeks or 4 weeks.

4. The method of claim 1, wherein the patient with anemia periodically receives peritoneal dialysis or hemodialysis.

5. The method of claim 1, wherein the administration is performed intravenously or subcutaneously.

6. The method of claim 1, wherein the method is to correct or maintain a blood hemoglobin level.

7. The method of claim 6, wherein the correction comprises administering the fusion polypeptide at a dose of 5 µg/kg or 8 µg/kg at an interval of 2 weeks; or administering the fusion polypeptide at a dose of 8 µg/kg at an interval of 4 weeks.

8. The method of claim 6, wherein the maintenance comprises administering the fusion polypeptide at a dose of 5 µg/kg or 8 µg/kg at an interval of 4 weeks.

9. The method of claim 6, comprising:
a) administering the fusion polypeptide to the patient with a blood hemoglobin level below normal range, at a dose of 5 µg/kg or 8 µg/kg at an interval of 2 weeks; or at a dose of 8 µg/kg at an interval of 4 weeks to correct the blood hemoglobin level to normal range; and
b) administering the fusion polypeptide to the patient having a blood hemoglobin level corrected to normal range through step a), at a dose of 5 µg/kg or 8 µg/kg at an interval of 4 weeks to maintain the blood hemoglobin level of normal range.

10. A method of correcting or maintaining a blood hemoglobin level of an anemia patient to a concentration of from 10 g/dL to 12 g/dL, comprising administering a fusion polypeptide to the anemia patient at a dose of from 5 µg/kg to 8 µg/kg at an interval of from 2 weeks to 4 weeks,
wherein the fusion polypeptide comprises an EPO and an immunoglobulin hybrid Fc, and
wherein the fusion polypeptide consists of the amino acid sequence of SEQ ID NO: 3,
wherein the anemia is due to a renal failure.

11. The method of claim 10, wherein the dose is 5 μg/kg or 8 μg/kg.

12. The method of claim 10, wherein the interval is 2 weeks or 4 weeks.

13. The method of claim 10, wherein the patient with anemia periodically receives peritoneal dialysis or hemodialysis.

14. The method of claim 10, wherein the administration is performed intravenously or subcutaneously.

15. The method of claim 10, wherein the correction comprises administering the fusion polypeptide at a dose of 5 μg/kg or 8 μg/kg at an interval of 2 weeks or at a dose of 8 μg/kg at an interval of 4 weeks.

16. The method of claim 10, wherein the maintenance comprises administering the fusion polypeptide at a dose of 5 μg/kg or 8 μg/kg at an interval of 4 weeks.

\* \* \* \* \*